(12) United States Patent
Ohta et al.

(10) Patent No.: US 7,593,507 B2
(45) Date of Patent: Sep. 22, 2009

(54) RADIATION IMAGE CAPTURING SYSTEM AND METHOD OF SETTING MINIMUM TRANSMISSION RADIO-FIELD INTENSITY IN SUCH RADIATION IMAGE CAPTURING SYSTEM

(75) Inventors: Yasunori Ohta, Kanagawa (JP); Eiichi Kito, Kanagawa (JP); Tsuyoshi Tanabe, Kanagawa (JP); Takuya Yoshimi, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/222,849

(22) Filed: Aug. 18, 2008

(65) Prior Publication Data

US 2009/0046834 A1 Feb. 19, 2009

(30) Foreign Application Priority Data

Aug. 16, 2007 (JP) ............................. 2007-212241
Jul. 4, 2008 (JP) ............................. 2008-175696

(51) Int. Cl.
H05G 1/64 (2006.01)
H05G 1/70 (2006.01)
G01D 18/00 (2006.01)

(52) U.S. Cl. ......................... 378/98.8; 378/91; 378/207

(58) Field of Classification Search ................ 378/98.8, 378/98, 91, 207, 116, 189, 190, 162, 165; 250/370.01, 370.08, 370.09

See application file for complete search history.

(56) References Cited

U.S. PATENT DOCUMENTS

| 7,298,825 | B2 * | 11/2007 | Omernick et al. | 378/116 |
|---|---|---|---|---|
| 7,324,628 | B2 * | 1/2008 | Liu et al. | 378/117 |
| 7,359,482 | B2 * | 4/2008 | Schmitt | 378/98.8 |
| 7,365,337 | B2 * | 4/2008 | Tsuchino et al. | 250/370.09 |
| 7,426,261 | B2 * | 9/2008 | Spahn | 378/98.8 |
| 7,474,731 | B2 * | 1/2009 | Spahn | 378/62 |
| 2003/0223540 | A1 * | 12/2003 | Hayashida et al. | 378/98.8 |

FOREIGN PATENT DOCUMENTS

| JP | 07-140255 | 6/1995 |
|---|---|---|
| JP | 2000-105297 | 4/2000 |
| JP | 2006-263339 | 10/2006 |

\* cited by examiner

*Primary Examiner*—Irakli Kiknadze
(74) *Attorney, Agent, or Firm*—Jean C. Edwards, Esq.; Akerman Senterfitt (57) ABSTRACT

When a cassette transceiver starts to transmit radiation image information to a console transceiver, the cassette transceiver transmits a test radio wave, and the console transceiver calculates a minimum transmission radio-field intensity of said cassette transceiver which is required to receive the radiation image information from a received intensity of said test radio wave, and transmits a command radio wave representing the calculated minimum transmission radio-field intensity as a command to said cassette transceiver. The cassette transceiver is thus capable of transmitting the radiation image information at the commanded minimum transmission radio-field intensity. The consumption of electric power for transmitting the radiation image information from the cassette transceiver to the console transceiver is thus minimized.

10 Claims, 11 Drawing Sheets

RADIATION IMAGE CAPTURING SYSTEM AND METHOD OF SETTING MINIMUM TRANSMISSION RADIO-FIELD INTENSITY IN SUCH RADIATION IMAGE CAPTURING SYSTEM

CROSS-REFERENCE TO RELATED APPLICATIONS

The present application claims priority from Japanese Patent Application Nos. 2007-212241, filed Aug. 16, 2007, and 2008-175696 filed Jul. 4, 2008, the contents of both of which are herein incorporated by reference in their entirety.

BACKGROUND OF THE INVENTION

1. Field of the Invention

The present invention relates to a radiation image capturing system including a cassette having a radiation detector for detecting a radiation that has passed through a subject and converting the detected radiation into radiation image information and an external controller for receiving the radiation image information transmitted from the cassette, and a method of setting a minimum transmission radio-field intensity in such a radiation image capturing system.

2. Description of the Related Art

In the medical field, there have widely been used radiation image capturing apparatus which apply a radiation to a subject and guide the radiation that has passed through the subject to a radiation detector so as to capture a radiation image from the radiation. Known forms of the radiation detector include a conventional radiation film for recording a radiation image by way of exposure, and a stimulable phosphor panel for storing a radiation energy representing a radiation image in a phosphor and reproducing the radiation image as stimulated light by applying stimulating light to the phosphor. The radiation film with the recorded radiation image is supplied to a developing device to develop the radiation image, or the stimulable phosphor panel is supplied to a reading device to read out the radiation image as a visible image.

In the operating room or the like, it is necessary to read a recorded radiation image immediately from a radiation detector after the radiation image is captured for the purpose of quickly and appropriately treating the patient. As a radiation conversion panel which meets such a requirement, there has been developed a radiation detector having a solid-state detector for converting a radiation directly into an electric signal or converting a radiation into visible light with a scintillator and then converting the visible light into an electric signal to read a detected radiation image.

Radiation image capturing systems employing such a radiation detector are disclosed in Japanese Patent No. 3494683 and Japanese Laid-Open Patent Publication No. 2006-263339.

In the radiation image capturing system disclosed in Japanese Patent No. 3494683, radiation image information detected by a radiation detector is transmitted to a processor by way of wireless communications, and signal processing such as image processing is performed on the radiation image information by the processor.

Japanese Laid-Open Patent Publication No. 2006-263339 reveals an electronic cassette which is capable of transmitting, by way of wireless communications, a large volume of radiation image data at a high rate using a high frequency in excess of 1 [GHz].

When the cassette transmits radiation image information to an external device by way of wireless communications, the cassette consumes a large amount of electric power. Accordingly, a battery incorporated in the cassette for energizing the cassette is relatively large in size, making the cassette large in volume and weight.

SUMMARY OF THE INVENTION

It is an object of the present invention to provide a radiation image capturing system which is capable of reducing the consumption of electric power required to transmit radiation image information from a cassette to an external device by way of wireless communications, for thereby saving electric power stored in a battery incorporated in the cassette, and a method of setting a minimum transmission radio-field intensity in such a radiation image capturing system.

A radiation image capturing system according to the present invention comprises a cassette and an external controller, the cassette having a radiation detector for detecting a radiation that has passed through a subject and converting the detected radiation into radiation image information, an image memory for storing the converted radiation image information, a first transceiver for transmitting the radiation image information stored in the image memory to the external controller by way of wireless communications at a transmission radio-field intensity based on a command radio wave from the external controller, and a battery for supplying electric power to the radiation detector and the first cassette transceiver, the external controller having a second transceiver for transmitting the command radio wave and receiving the radiation image information transmitted from the cassette.

When the first transceiver starts to transmit the radiation image information to second transceiver, the first transceiver transmits a test radio wave, and the second transceiver calculates a minimum transmission radio-field intensity of the first transceiver which is required to receive the radiation image information, from a received intensity of the test radio wave, and transmits the command radio wave representing a command indicative of the calculated minimum transmission radio-field intensity to the first transceiver. The first transceiver is thus capable of transmitting the radiation image information at the minimum transmission radio-field intensity based on the command radio wave. As a result, the consumption of electric power required to transmit the radiation image information from the first transceiver of the cassette to the second transceiver of the external controller is minimized, and the battery power is saved.

The second transceiver may transmit the command radio wave representing the command indicative of at a radio-field intensity representative of the sum of the calculated minimum transmission radio-field intensity and a given radio-field intensity, to the first transceiver. The first transceiver is thus capable of transmitting the radiation image information at the radio-field intensity representative of the sum of the calculated minimum transmission radio-field intensity and the given radio-field intensity, based on the command radio wave. The first transceiver can transmit the radiation image information more stably and reliably while saving electric power stored in the battery.

The cassette may include a power supply switch, and the first transceiver may transmit the test radio wave when the power supply switch is turned on. When the power supply switch is turned on, it is highly likely for the radiation image capturing system to start capturing a radiation image. By confirming the radio-field intensity when a radiation image is to be captured, the first transceiver can transmit the radiation image information more reliably to the second transceiver.

If the power supply switch has been turned on, the cassette may turn off the power supply switch when the first transceiver finishes transmitting the radiation image information to second transceiver. The battery power is thus saved more effectively.

According to the present invention, there is also provided a method of setting a minimum transmission radio-field intensity in a radiation image capturing system when a cassette transceiver of a cassette having a radiation detector for detecting a radiation that has passed through a subject and converting the detected radiation into radiation image information starts to transmit the radiation image information to a console transceiver of a console, the method comprising the steps of transmitting a test radio wave from the cassette transceiver, calculating, in the console transceiver, a minimum transmission radio-field intensity of the cassette transceiver which is required to receive the radiation image information from a received intensity of the test radio wave, and transmitting a command radio wave representing the calculated minimum transmission radio-field intensity as a command from the console transceiver to the cassette transceiver, and setting a transmission radio-field intensity of the cassette transceiver to the minimum transmission radio-field intensity when the cassette transceiver receives the command radio wave, for transmitting the radiation image information at the minimum transmission radio-field intensity from the cassette transceiver to the console transceiver. Consequently, the consumption of electric power required to transmit the radiation image information from the first transceiver to the second transceiver is minimized, and the battery power is saved.

According to the present invention, for transmitting the radiation image information from the cassette to the external controller such as a console or the like, the minimum transmission radio-field intensity required to transmit the radiation image information is calculated. The consumption of electric power to transmit the radiation image information is thus minimized, and the battery power for energizing the cassette is saved.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Like or corresponding parts are denoted by lines or corresponding reference characters throughout views.

Figure 1:
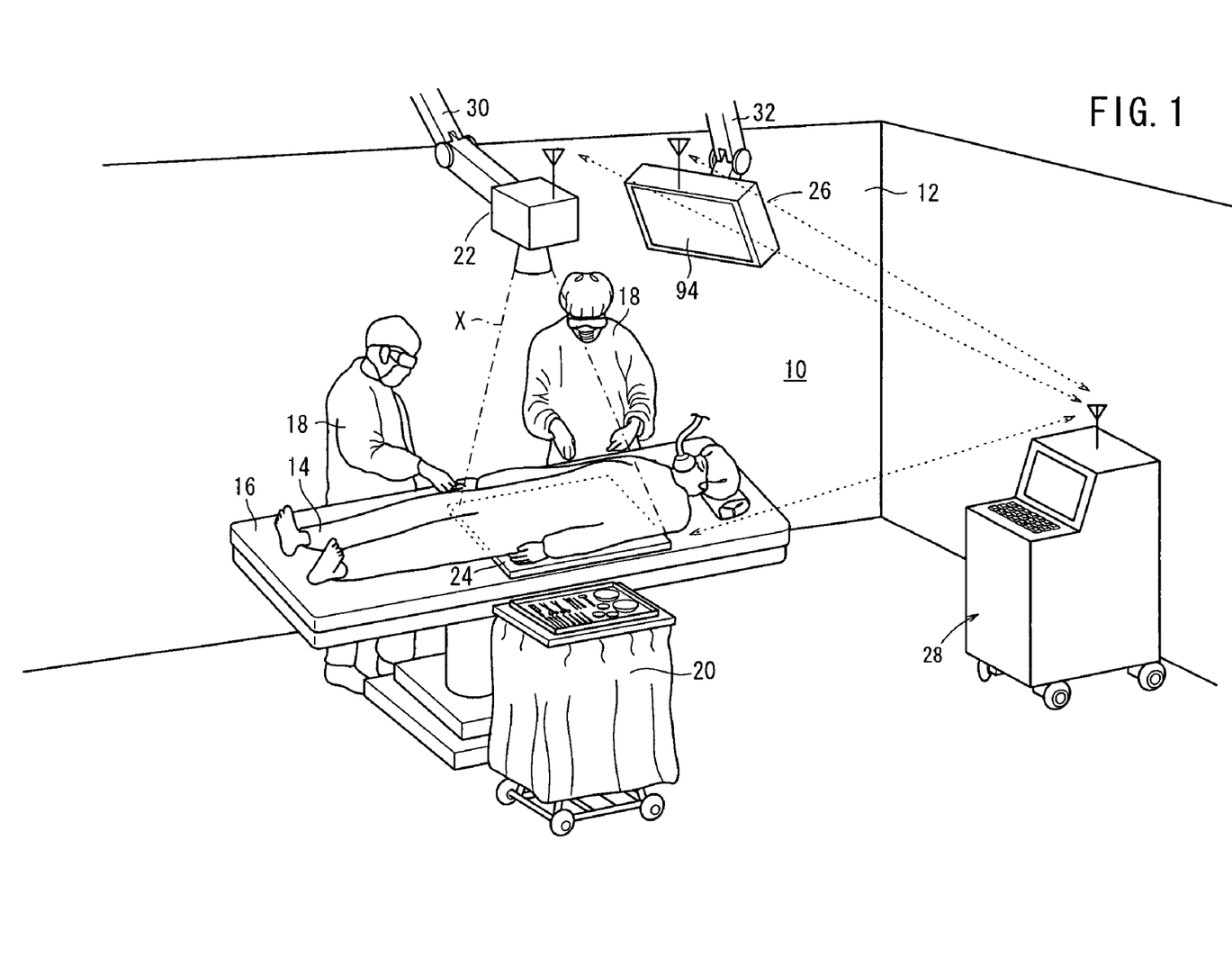
FIG. 1 is a perspective view of an operating room incorporating a radiation image capturing system according to an embodiment of the present invention.

As shown in FIG. 1, an operating room 12 incorporates a radiation image capturing system 10 according to a first embodiment of the present invention. The operating room 12 has, in addition to the radiation image capturing system 10, a surgical table (bed) 16 for a patient 14 to lie thereon, and an instrument table 20 disposed on one side of the surgical table 16 for placing thereon various tools and instruments to be used by surgeons 18 for operating the patient 14. The surgical table 16 is surrounded by various apparatus required for surgical operations, including an anesthesia apparatus, an aspirator, an electrocardiograph, a blood pressure monitor, etc.

The radiation image capturing system 10 includes an image capturing apparatus 22 for irradiating the patient 14 as a subject with a radiation X at a dose according to image capturing conditions, a cassette (radiation detecting cassette) 24 housing therein a radiation detector, to be described later, for detecting the radiation X that has passed through the patient 14, a display device 26 for displaying a radiation image based on the radiation X that is detected by the radiation detector, and a console (external controller for the cassette 24) 28 for controlling the image capturing apparatus 22, the cassette 24, and the display device 26. The console 28, the image capturing apparatus 22, the cassette 24, and the display device 26 send and receive signals by way of wireless communications indicated by the broken lines.

The image capturing apparatus 22 is coupled to a universal arm 30 so as to be movable to a desired position for capturing a desired area of the patient 14 and also to be retractable to a position where a surgical operation on the patient 14 by the surgeons 18 is not disturbed. Similarly, the display device 26 is coupled to a universal arm 32 so as to be movable to a position where the surgeons 18 can easily confirm a captured radiation image displayed on the display device 26.

Figure 2:
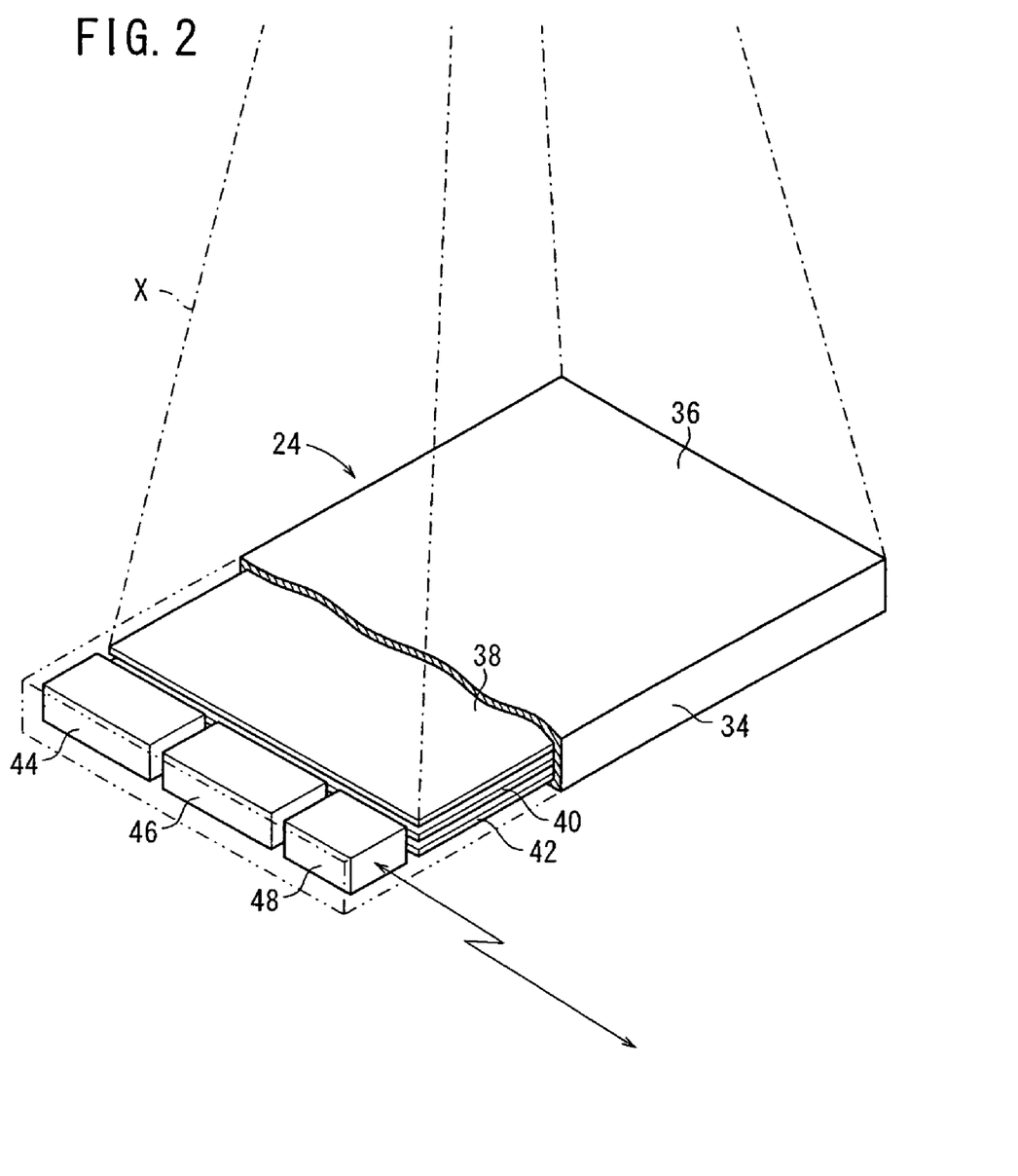
FIG. 2 is a perspective view, partly cut away, showing internal structural details of a cassette used in the radiation image capturing system.

FIG. 2 shows in perspective internal structural details of the cassette 24. As shown in FIG. 2, the cassette 24 has a casing 34 made of a material permeable to the radiation X. The casing 34 houses therein a grid 38 for removing scattered rays of the radiation X from the patient 14, a radiation detector 40 for detecting the radiation X that has passed through the patient 14, and a lead plate 42 for absorbing back scattered rays of the radiation X, which are successively arranged in that order from a irradiated surface 36 of the casing 34 which is irradiated with the radiation X. The irradiated surface 36 of the casing 34 may be constructed as the grid 38.

The casing 34 also houses therein a battery 44 having a voltage Vcc as a power supply of the cassette 24, a cassette controller 46 for energizing the radiation detector 40 with electric power supplied from the battery 44, and a cassette transceiver (first transceiver) 48 for sending and receiving signals including the information of the radiation X detected by the radiation detector 40, to and from the console 28. A shield plate of lead or the like should preferably be placed over the side surfaces of the cassette controller 46 and the cassette transceiver 48 under the irradiated surface 36 of the casing 34 to protect the cassette controller 46 and the cassette transceiver 48 against damage which would otherwise be caused if irradiated with the radiation X.

Figure 3:
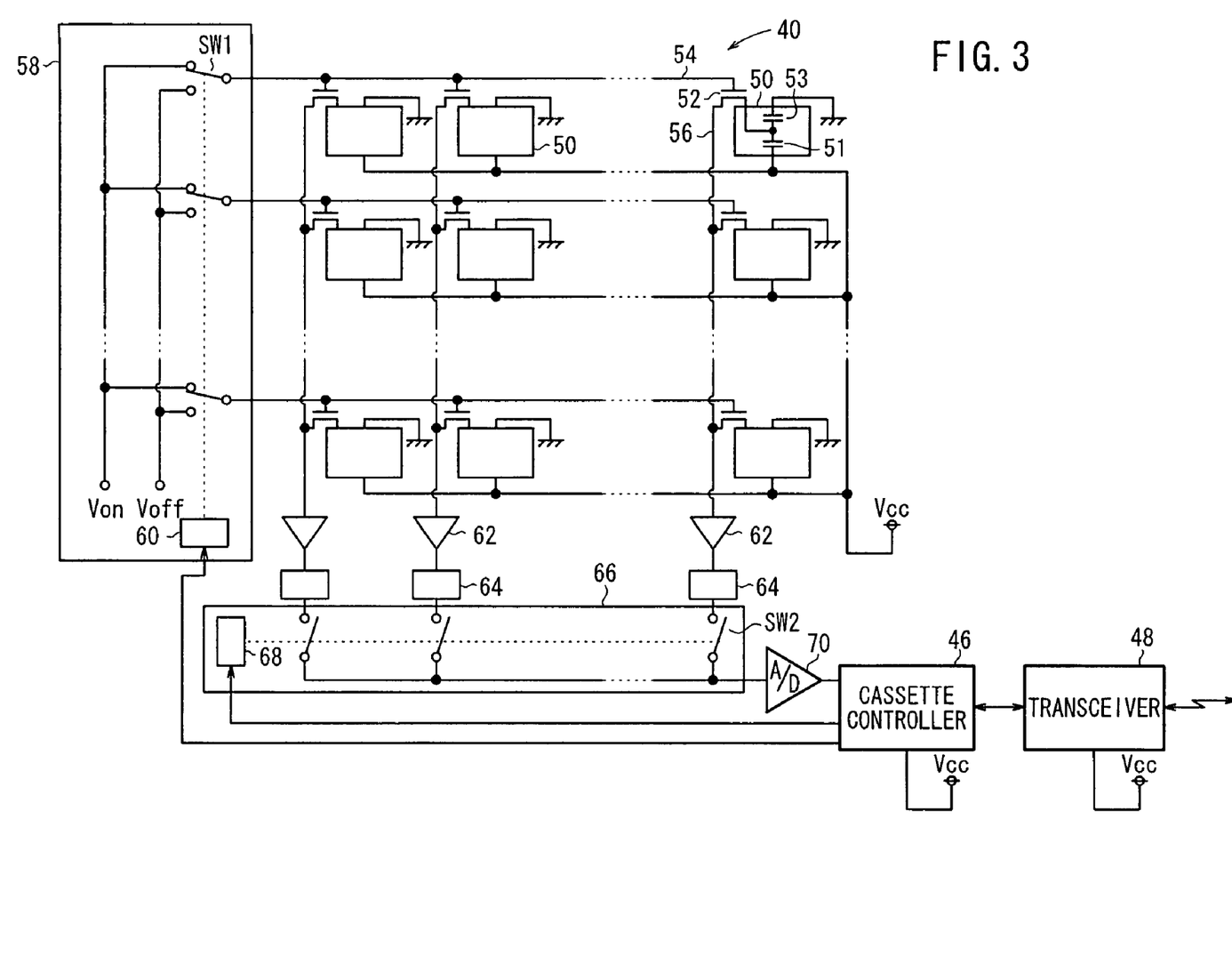
FIG. 3 is a block diagram of a circuit arrangement of a radiation detector of the cassette shown in FIG. 2.

FIG. 3 shows in block form a circuit arrangement of the radiation detector 40. As shown in FIG. 3, the radiation detector 40 comprises an array of thin-film transistors (TFTs) 52 arranged in rows and columns, a photoelectric conversion layer 51 made of a material such as amorphous selenium (a-Se) for generating electric charges upon detection of the radiation X, the photoelectric conversion layer 51 being disposed on the array of TFTs 52, and an array of storage capacitors 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are turned on along each row at a time to read the electric charges from the storage capacitors 53 as an image signal. In FIG. 3, the photoelectric conversion layer 51 and one of the storage capacitors 53 are shown as a pixel 50, and the pixel 50 is connected to one of the TFTs 52. Details of the other pixels 50 are omitted from illustration. Since amorphous selenium tends to change its structure and lose its function at high temperatures, it needs to be used in a certain temperature range. Therefore, some means for cooling the radiation detector 40 should preferably be provided in the cassette 24.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff for turning on and off the TFTs 52 along the rows, from the line scanning driver 58. The line scanning driver 58 comprises a plurality of switches SW1 for switching between the gate lines 54 and an address decoder 60 for outputting a selection signal for selecting one of the switches SW1. The address decoder 60 is supplied with an address signal from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of switches SW2 for successively switching between the signal lines 56 and an address decoder 68 for outputting a selection signal for selecting one of the switches SW2. The address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image information, which is supplied to the cassette controller 46.

Figure 4:
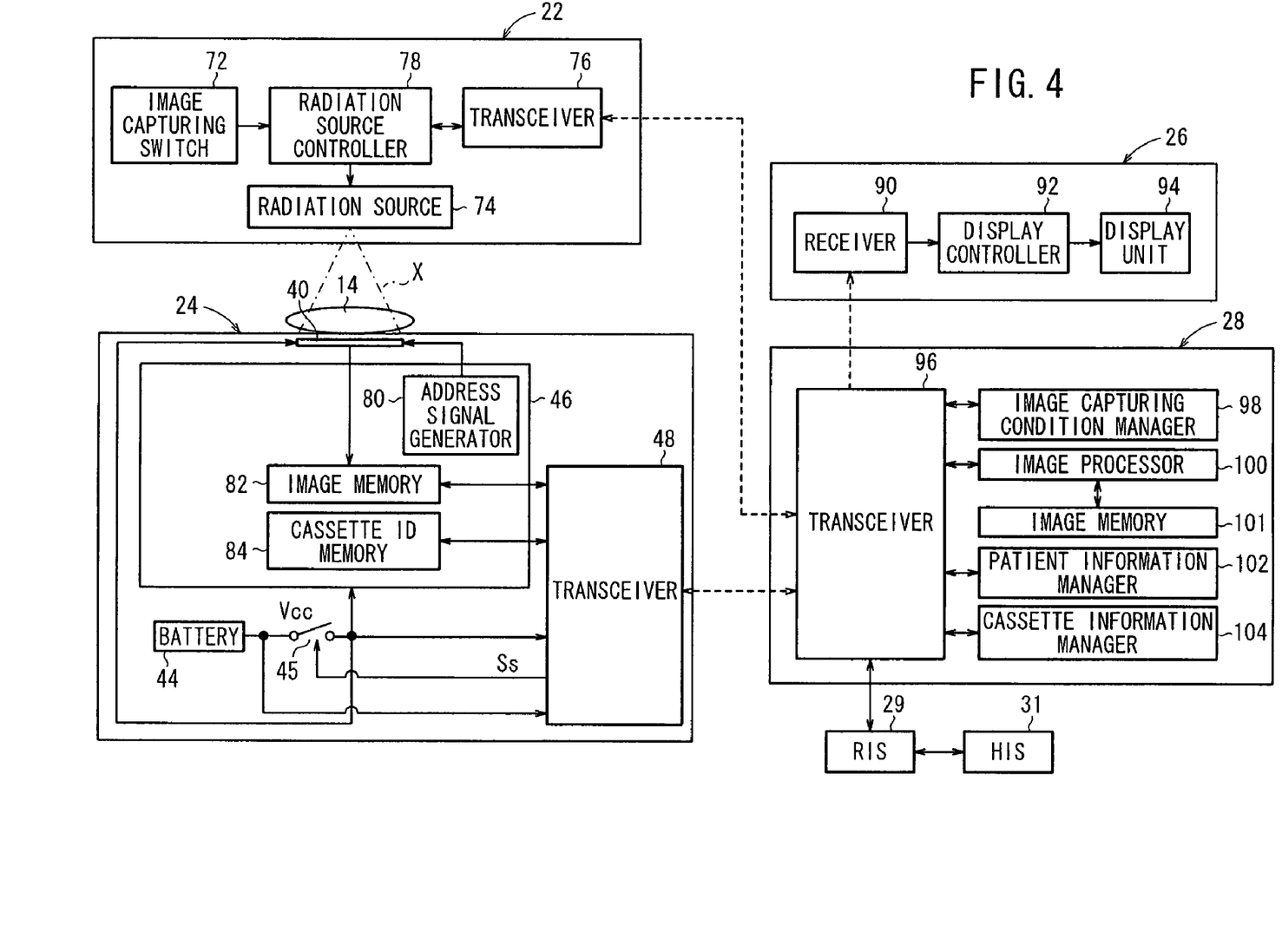
FIG. 4 is a block diagram of the radiation image capturing system.

FIG. 4 shows in block form the radiation image capturing system 10 which comprises the image capturing apparatus 22, the cassette 24, the display device 26, and the console 28. The console 28 is connected to a radiology information system (RIS) 29 which generally manages radiation image information handled by the radiological department of the hospital and other information. The RIS 29 is connected to a hospital information system (HIS) 31 which generally manages medical information in the hospital.

The image capturing apparatus 22 comprises an image capturing switch 72, a radiation source 74 for outputting the radiation X, a transceiver 76 for receiving image capturing conditions from a console transceiver 96 of the console 28 by way of wireless communications and transmitting an image capturing completion signal, etc. to the console 28 by way of wireless communications, and a radiation source controller 78 for controlling the radiation source 74 based on an image capturing start signal supplied from the image capturing switch 72 and image capturing conditions supplied from the transceiver 76.

The cassette 24 houses therein the radiation detector 40, the battery 44, the cassette controller 46, the cassette transceiver 48, and a power supply switch 45. The power supply switch 45 is selectively turned on and off either manually or by a switch control signal Ss from the cassette transceiver 48 to selectively supply and stop electric power from the battery 44 to the radiation detector 40, the cassette controller 46, and the cassette transceiver 48. The battery 44 is directly connected to the cassette transceiver 48 which has a sleep and wake-up function, and supplies standby electric power (low electric power) to the cassette transceiver 48 when it is in a sleep mode.

The cassette controller 46 comprises an address signal generator 80 for supplying address signals to the address decoder 60 of the line scanning driver 58 and the address decoder 68 of the multiplexer 66 of the radiation detector 40, an image memory 82 for storing the radiation image information detected by the radiation detector 40, and a cassette ID memory 84 for storing cassette ID information for identifying the cassette 24.

The cassette transceiver 48 receives a command radio wave, to be described later from the console 28 by way of wireless communications and transmits the cassette ID information stored in the cassette ID memory 84 and the radiation image information stored in the image memory 82 to the console 28 by way of wireless communications.

The display device 26 comprises a receiver 90 for receiving compressed radiation image information from the console 28, a display controller 92 for controlling the display of the received radiation image information, and a display unit 94 for displaying the radiation image information processed by the display controller 92.

The console 28 comprises a console transceiver (second transceiver) 96 for transmitting and receiving necessary information including radiation image information to and from the image capturing apparatus 22, the cassette 24, and the display device 26 by way of wireless communications, an image capturing condition manager 98 for managing image capturing conditions required for the image capturing apparatus 22 to capture radiation images, an image processor (image processing means) 100 for processing radiation image information transmitted from the cassette 24, an image memory 101 for storing the radiation image information processed by the image processor 100, a patient information manager 102 for managing patient information of the patient 14 whose images are to be captured, and a cassette information manager 104 for managing cassette information, corresponding to the radiation image information, transmitted from the cassette 24. The console 28 may be located outside of the operating room 12 insofar as it can transmit and receive signals to and from the device 26 by way of wireless communications.

The image capturing conditions refer to condition for determining a tube voltage, a tube current, an irradiation time, etc. required to apply a radiation X at an appropriate dose to an area to be imaged of the patient 14. The image capturing conditions may include an area to be imaged of the patient 14, an image capturing method, etc., for example. The patient information refers to information for identifying the patient 14, such as the name, gender, patient ID number, etc. of the patient 14. Ordering information for instructing the radiation image capturing system 10 to capture a radiation image, including the image capturing conditions and the patient information, can be set directly on the console 28 or can be supplied from an external source to the console 28 via the RIS 29. The cassette information refers to cassette ID information for identifying the cassette 24.

Figure 5:
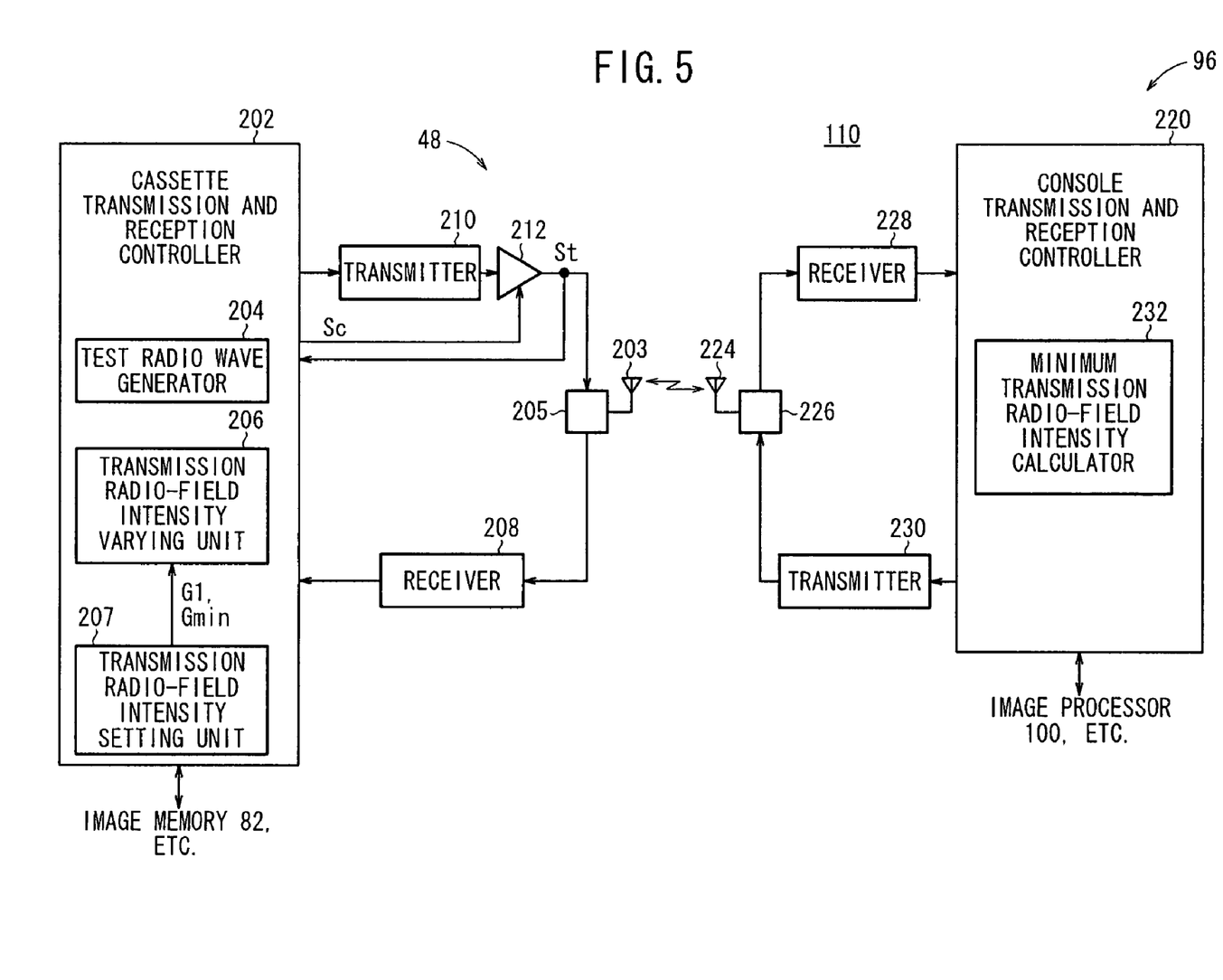
FIG. 5 is a block diagram of a radiation image information transmitting and receiving system.

FIG. 5 shows in block form a radiation image information transmitting and receiving system 110 made up of some components of the cassette transceiver 48 and the console transceiver 96.

As shown in FIG. 5, the cassette transceiver 48 comprises a cassette transmission and reception controller 202 having a microcomputer, an antenna 203, an antenna sharing unit 205, a receiver 208, a transmitter 210, and a variable-gain amplifier 212.

The cassette transmission and reception controller 202 comprises a test radio wave generator 204, a transmission radio-field intensity varying unit 206, and a transmission radio-field intensity setting unit 207.

The receiver 208 receives a radio wave (RF signal) received by the antenna 203 through the antenna sharing unit 205, converts the RF signal into an intermediate-frequency signal (IF signal), demodulates the IF signal, and sends the demodulated IF signal as reception data to the cassette transmission and reception controller 202. The transmitter 210 modulates data (radiation image information) read from the image memory 82 (see FIG. 4) or a test signal (a signal representative of a test radio wave) output from the test radio wave generator 204, and converts the modulated signal from an IF signal into an RF signal. The test radio wave has a transmission radio-field intensity which is represented by a predetermined multiple of the normal transmission radio-field intensity so that the console transceiver 96 can receive the test radio wave.

When the test radio wave generator 204 detects a turned-on state of the power supply switch 45, the test radio wave generator 204 supplies a test signal to the transmitter 210.

The radio-field intensities of the test radio wave and the transmission radio wave for the radiation image information are set in the transmission radio-field intensity setting unit 207. The transmission radio-field intensity varying unit 206 outputs a variable-gain control signal Sc depending on the transmission radio-field intensity set by the transmission radio-field intensity setting unit 207 to a gain control port of the variable-gain amplifier 212.

The variable-gain amplifier 212 outputs a transmission signal St for an electric power level corresponding to the set transmission radio-field intensity set. The transmission signal St is delivered through the antenna sharing unit 205 to the antenna 203, which transmits a transmission radio wave (a test radio wave or a radio wave including radiation image information) represented by the transmission signal St.

The console transceiver 96 comprises a console transmission and reception controller 220 having a microcomputer, an antenna 224, an antenna sharing unit 226, a receiver 228, and a transmitter 230.

The transmission and reception controller 220 comprises a minimum transmission radio-field intensity calculator 232. The receiver 228 receives a radio wave (RF signal) received by the antenna 224 through the antenna sharing unit 226, converts the RF signal into an intermediate-frequency signal (IF signal), demodulates the IF signal, and sends the demodulated IF signal as reception data to the console transmission and reception controller 220. The demodulated reception data contain a test signal or radiation image information.

When the minimum transmission radio-field intensity calculator 232 receives the test radio wave, it calculates a minimum transmission radio-field intensity of the cassette transceiver 48 depending on the received intensity of the test radio wave, and supplies the calculated minimum transmission radio-field intensity as a command signal to the transmitter 230. The transmitter 230 transmits the command signal through the antenna sharing unit 226 to the antenna 224, which transmits a command radio wave represented by the command signal.

Figure 6A:
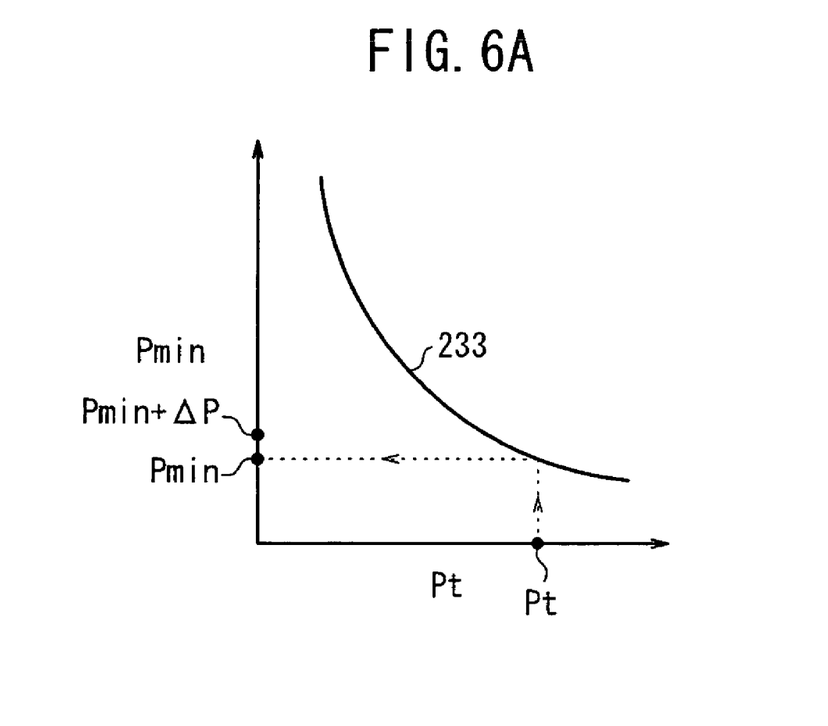
FIG. 6A is a diagram illustrative of a calculating process performed by a minimum transmission radio-field intensity calculator in the radiation image information transmitting and receiving system shown in FIG. 5.

FIG. 6A is illustrative of a calculating process performed by the minimum transmission radio-field intensity calculator 232. A characteristic curve 233 representing the minimum transmission radio-field intensity Pmin of the cassette transceiver 48, which corresponds to the received intensity Pt of the test radio wave received by the console transceiver 96, is measured in advance, and stored as a table (map), a computational equation, or the like, in a memory of the transmission and reception controller 220. Therefore, a minimum transmission radio-field intensity Pmin to be set in the cassette transceiver 48 depending on the received intensity Pt of the test radio wave can immediately be determined from the characteristic curve 233. The received intensity Pt and the minimum transmission radio-field intensity Pmin are essentially inversely proportional to each other. The minimum transmission radio-field intensity Pmin represents a minimum level at which stable wireless communications can be performed between the cassette transceiver 48 and the console transceiver 96.

Figure 7:
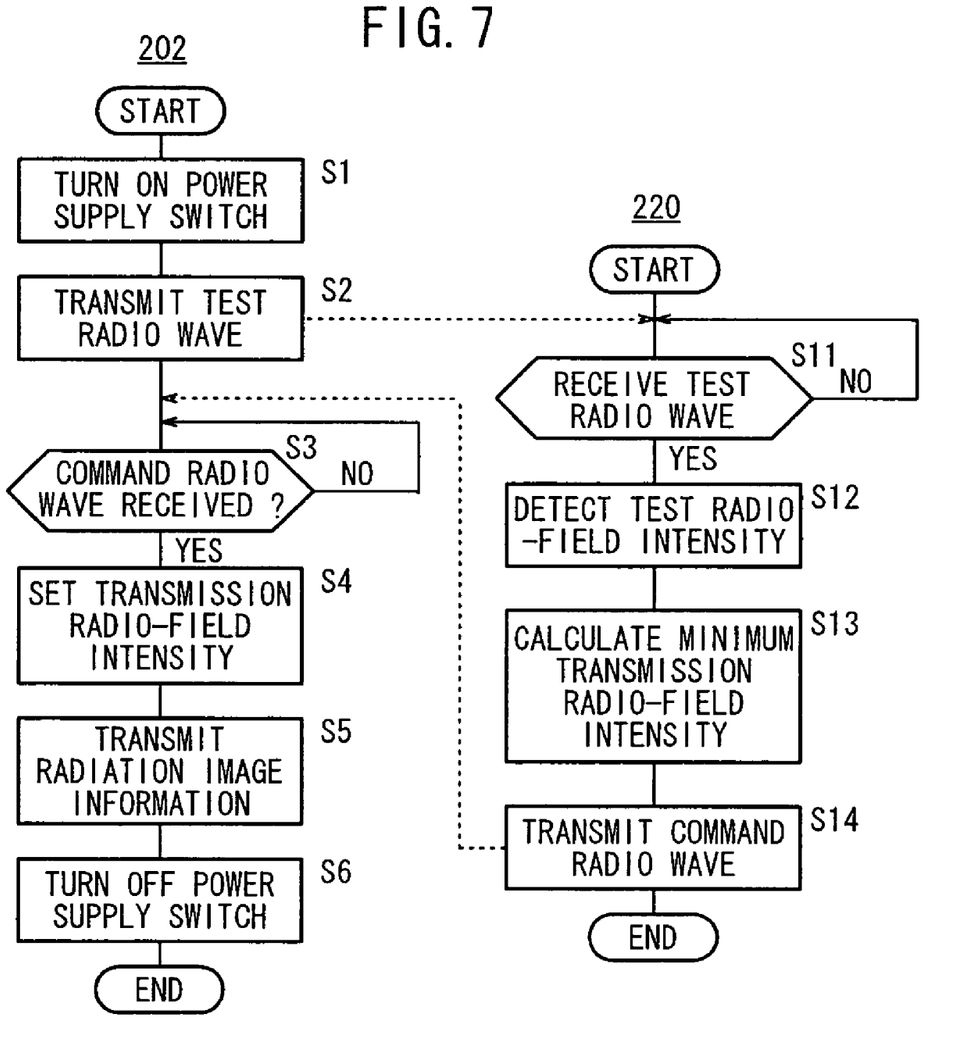
FIG. 7 is a flowchart of an operation sequence of the radiation image capturing system.

The radiation image capturing system 10 according to the present embodiment, which incorporates the radiation image information transmitting and receiving system 110 (FIG. 5), is basically constructed as described above, and operation of the radiation image capturing system 10 will be described below with reference to a flowchart shown in FIG. 7.

The radiation image capturing system 10 is installed in the operating room 12 and used when a radiation image of the patient 14 is required by the surgeons 18 who are performing a surgical operation on the patient 14. Before a radiation image of the patient 14 is captured, patient information of the patient 14 to be imaged is registered in the patient information manager 102 of the console 28. If an area to be imaged of the patient 14 and an image capturing method have already been known, they are registered as image capturing conditions in the image capturing condition manager 98. After the above preparatory process is finished, the surgeons 18 perform a surgical operation on the patient 14.

For capturing a radiation image of the patient 14 during the surgical operation, one of the surgeons 18 or the radiological technician places the cassette 24 between the patient 14 and the surgical table 16, with the irradiated surface 36 facing the image capturing apparatus 22. Then, one of the surgeons 18 or the radiological technician turns on the power supply switch 45.

In step S1, the cassette transmission and reception controller 202 of the cassette transceiver 48 detects when the power supply switch 45 is turned on.

In step S2, the test radio wave generator 204 of the cassette transmission and reception controller 202 sets a gain G1 for transmitting a test radio wave having a predetermined intensity greater than the normal transmission radio-field intensity in the transmission radio-field intensity setting unit 207. The transmission radio-field intensity varying unit 206 supplies the gain G1 set in the transmission radio-field intensity setting unit 207 to the gain control port of the variable-gain amplifier 212.

The test radio wave generator 204 generates and outputs a test signal comprising a unique word to the transmitter 210. The test signal is amplified with the gain G1 by the variable-gain amplifier 212, producing a transmission signal St corresponding to a test signal intensity (a radio wave having the predetermined intensity). The transmission signal St is supplied through the antenna sharing unit 205 to the antenna 203, which transmits transmission radio wave represented by the transmission signal St from the cassette transceiver 48.

In step S11, if the console transmission and reception controller 220 of the console transceiver 96 receives a test radio wave (a radio wave corresponding to the test radio wave of the predetermined intensity greater than the normal transmission radio-field intensity) via the antenna 224, the antenna sharing unit 226, and the receiver 228, then the console transmission and reception controller 220 detects the intensity (received intensity) Pt of the received test radio wave in step S12.

In step S13, the minimum transmission radio-field intensity calculator 232 of the transmission and reception controller 220 refers to the characteristic curve 233 shown in FIG. 6A, and calculates a minimum transmission radio-field intensity Pmin (at the broken-line position on the vertical axis shown in FIG. 6A) corresponding to the received intensity Pt (at the broken-line position on the horizontal axis shown in FIG. 6A) of the test radio wave.

In step S14, the console transmission and reception controller 220 generates a command signal representing the calculated minimum transmission radio-field intensity Pmin as a command (contents), and supplies the command signal through the transmitter 230 and the antenna sharing unit 226 to the antenna 224, which transmits a command radio wave represented by the command signal.

In step S3, the cassette transmission and reception controller 202 of the cassette transceiver 48 receives the command radio wave.

In step S4, the cassette transmission and reception controller 202 sets the contents of the received command radio wave, i.e., a gain (Gmin) depending on the minimum transmission radio-field intensity Pmin to be set in itself, in the transmission radio-field intensity setting unit 207.

The transmission radio-field intensity varying unit 206 sets a variable-gain control signal Sc corresponding to the gain Gmin set in the transmission radio-field intensity setting unit 207, in the variable-gain amplifier 212.

When radiation image information to be described later is transmitted as a signal radio wave from the cassette 24 in step S5, therefore, the intensity of the transmitted signal radio wave is held to a minimum level (required minimum level), thereby reducing the consumption of electric power of the battery 44 of the cassette 24.

In calculating the test radio-field intensity in step S13, a value representing the sum of the calculated minimum transmission radio-field intensity Pmin and a certain value (excess radio-field intensity) ΔP may be set as a minimum transmission radio-field intensity (Pmin+ΔP) (see FIG. 6A). With the minimum transmission radio-field intensity (Pmin+ΔP) thus set, it is possible to transmit the radiation image information more stably and reliably while at the same time saving electric power stored in the battery 44.

Then, after having moved the image capturing apparatus 22 to a position confronting the cassette 24, one of the surgeons 18 or the radiological technician turns on the image capturing switch 72 to capture a radiation image of the patient 14.

The radiation source controller 78 of the image capturing apparatus 22 acquires the image capturing conditions about the area to be imaged of the patient 14 by way of wireless communications from the image capturing condition manager 98 of the console 28 via the console transceiver 96 and the transceiver 76 of the image capturing apparatus 22. When the radiation source controller 78 receives the image capturing conditions, it controls the radiation source 74 to apply a radiation X at a given dose to the patient 14 according to the image capturing conditions.

The radiation X which has passed through the patient 14 is applied to the grid 38 of the cassette 24, which removes scattered rays of the radiation X. Then, the radiation X is applied to the radiation detector 40, and converted into electric signals by the photoelectric conversion layer 51 of the pixels 50 of the radiation detector 40. The electric signals are stored as electric charges in the storage capacitors 53 (see FIG. 3). The stored electric charges, which represent radiation image information of the patient 14, are read from the storage capacitors 53 according to address signals which are supplied from the address signal generator 80 of the cassette controller 46 to the line scanning driver 58 and the multiplexer 66.

Specifically, in response to the address signal supplied from the address signal generator 80, the address decoder 60 of the line scanning driver 58 outputs a selection signal to select one of the switches SW1, which supplies the control signal Von to the gates of the TFTs 52 connected to the gate line 54 corresponding to the selected switch SW1. In response to the address signal supplied from the address signal generator 80, the address decoder 68 of the multiplexer 66 outputs a selection signal to successively turn on the switches SW2 to switch between the signal lines 56 for thereby reading the electric charges stored in the storage capacitors 53 of the pixels 50 connected to the selected gate line 54, which is selected by the line scanning driver 58, through the signal lines 56.

The electric charges, representing radiation image information, read from the storage capacitors 53 of the pixels 50 connected to the selected gate line 54 are amplified by the respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal which represents the radiation image information is stored in the image memory 82 (see FIG. 4) of the cassette controller 46.

Similarly, the address decoder 60 of the line scanning driver 58 successively turns on the switches SW1 to switch between the gate lines 54 according to the address signal supplied from the address signal generator 80. The electric charges, representing radiation image information, stored in the storage capacitors 53 of the pixels 50 connected to the successively selected gate lines 54 are read through the signal lines 56, and processed by the multiplexer 66 and the A/D converter 70 into digital signals, which are stored in the image memory 82 of the cassette controller 46.

In step S5, the radiation image information stored in the image memory 82 is read from the image memory 82 and supplied through the cassette transmission and reception controller 202 of the cassette transceiver 48, the transmitter 210, the variable-gain amplifier 212, and the antenna sharing unit 205 to the antenna 203, which transmits a radio wave at a predetermined radio-field intensity. The predetermined radio-field intensity is equal to the minimum transmission radio-field intensity Pmin of the transmission signal St amplified by the variable-gain amplifier 212 or the transmission radio-field intensity Pmin+ΔP which includes the extra radio-field intensity ΔP, based on the variable-gain control signal Sc corresponding to the gain Gmin that has been set in the control port of the variable-gain amplifier 212 by the transmission radio-field intensity setting unit 207 in step S4.

The radiation image information transmitted from the cassette transceiver 48 of the cassette 24 to the console 28 is received by the antenna 224 of the console transceiver 96 and supplied through the antenna sharing unit 226 and the receiver 228 to the console transmission and reception controller 220. The radiation image information is then processed by the image processor 100, and then stored in the image memory 101 of the console 28 in association with the patient information of the patient 14 registered in the patient information manager 102.

The radiation image information processed by the image processor 100 is read out from the image memory 101 and transmitted from the console transceiver 96 to the display device 26. In the display device 26, the receiver 90 receives the radiation image information, and the display controller 92 controls the display unit 94 to display a radiation image based on the radiation image information.

Since the radiation image of the patient 14 captured during the surgical operation is quickly displayed on the display unit 94, the surgeons 18, the radiological technician, and other staff members find the displayed radiation image highly useful.

When the cassette transmission and reception controller 202 confirms the end of the transmission of the radiation image information in step S5, the cassette transmission and reception controller 202 outputs a switch control signal Ss (see FIG. 4) to turn off the power supply switch 45 in step S6. Accordingly, the cassette 24 is prevented from being left with the power supply switch 45 being turned on, i.e., with a certain amount of electric power being continuously consumed. The cassette 24 is thus controlled to save electric power. Though the power supply switch 45 is turned off, since the battery 44 supplies electric power to the cassette transmission and reception controller 202 of the cassette transceiver 48, (the CPU of) the cassette transmission and reception controller 202 is held in a standby mode with a standby amount of electric power which is considerably smaller than the above certain amount of electric power.

According to the present embodiment, as described above, the radiation image capturing system 10 includes the cassette 24 and the console 28 as an external controller, the cassette 24 having the radiation detector 40 for detecting the radiation X that has passed through the patient 14 and converting the detected radiation into radiation image information, the image memory 82 for storing the converted radiation image information, the cassette transceiver 48 as the first transceiver for transmitting the radiation image information stored in the image memory 82 to the external controller by way of wireless communications at a transmission radio-field intensity corresponding to a command radio wave from the external device, and the battery 44 for supplying electric power to the radiation detector 40 and the cassette transceiver 48, the console 28 having the console transceiver 96 for transmitting the command radio wave and receiving the radiation image information transmitted from the cassette 24 at the transmission radio-field intensity depending on the command radio wave. When the cassette transceiver 48 starts to transmit the radiation image information to the console transceiver 96, the cassette transceiver 48 transmits a test radio wave, and the console transceiver 96 calculates a minimum transmission radio-field intensity Pmin of the cassette transceiver 48 which is required to receive the radiation image information based on a received intensity Pt of the test radio wave, and transmits the command radio wave representing a command indicative of the calculated minimum transmission radio-field intensity Pmin to the cassette transceiver 48. The cassette transceiver 48 is thus capable of transmitting the radiation image information at the commanded minimum transmission radio-field intensity Pmin. Therefore, the consumption of electric power required for transmitting the radiation image information from the cassette transceiver 48 to the console transceiver 96 can be minimized, and as a result the battery power of the cassette 24 can be saved.

If the console transceiver 96 transmits the command radio wave having as its command a radio-field intensity representing the sum of the calculated minimum transmission radio-field intensity Pmin and a certain radio-field intensity ΔP, to the cassette transceiver 48, then the cassette transceiver 48 transmits the radiation image information at the radio-field intensity (Pmin+ΔP) which represents the sum of the minimum transmission radio-field intensity Pmin and the certain extra radio-field intensity ΔP. The cassette transceiver 48 can thus transmit the radiation image information more stably and reliably while at the same time saving electric power stored in the battery.

The test radio wave is transmitted when the power supply switch 45 of the cassette 24 is turned on. Therefore, when the radiation image information is stored in the image memory 82 of the cassette 24, the radiation image information is reliably transmitted to the console transceiver 96. When the transmission of the radiation image information is finished, the power supply switch 45 is turned off. The battery 44 thus serves as a more effective power saver.

According to the present embodiment, inasmuch as the consumption of electric power is minimized while transmitting the radiation image information from the cassette 24 to the console 28, electric power of the battery 44 for energizing the cassette 24 is saved.

Figure 6B:
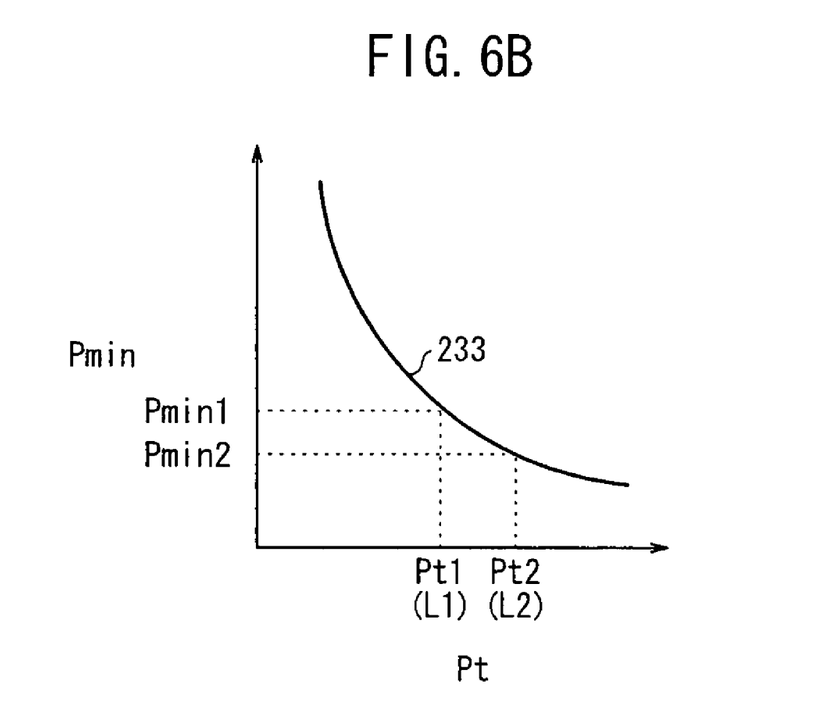
FIG. 6B is a diagram illustrative of the calculation of the minimum transmission radio-field intensities of cassette transceivers of two cassettes according to the calculating process illustrated in the diagram shown in FIG. 6A.
Figure 8:
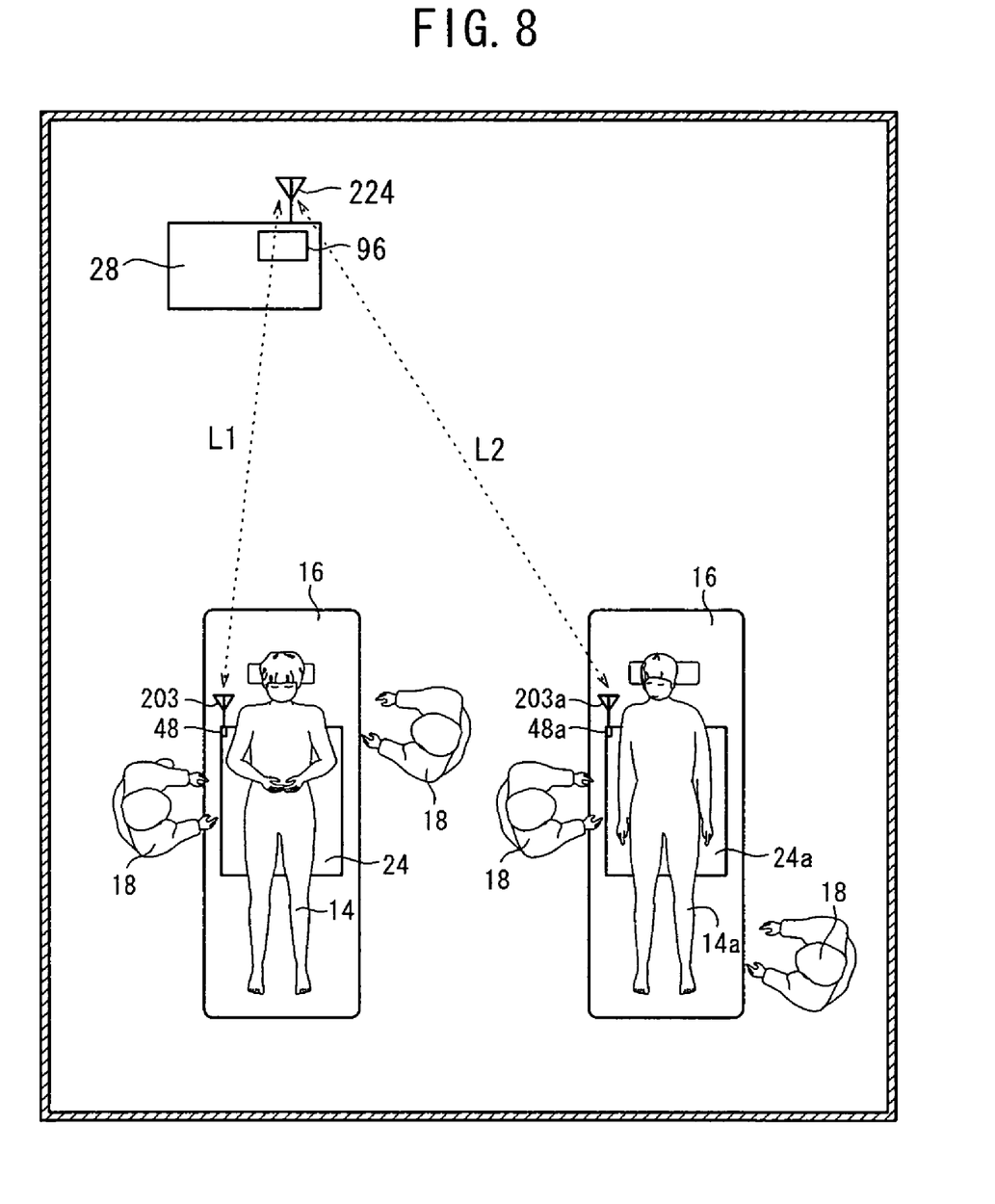
FIG. 8 is a plan view of an operating room incorporating a radiation image capturing system according to another embodiment of the present invention.

FIG. 8 shows in plan an operating room incorporating a radiation image capturing system according to another embodiment of the present invention. In the operating room shown in FIG. 8, radiation image information of patients 14, 14a is transmitted from cassette transceivers 48, 48a of respective cassettes 24, 24a placed beneath the respective patients 14, 14a and received by the console transceiver 96 of the console 28 during an organ transplant operation. In the radiation image capturing system, minimum transmission radio-field intensities Pmin1, Pmin2 depending on respective transmission radio-field intensities Pt1, Pt2 (see FIG. 6B) based respectively on a spatial length (radio wave propagation length) L1 between an antenna 203 of the cassette 24 and an antenna 224 of the console 28 and a spatial length (radio wave propagation length) L2 between an antenna 203a of the cassette 24a and the antenna 224 of the console 28, are set in the respective transmission radio-field intensity setting units 207 of the cassettes 24, 24a. With the minimum transmission radio-field intensities Pmin1, Pmin2 being thus set, the cassette transceivers 48, 48a can transmit the radiation image information at a minimum required level of consumed electric power from the batteries 44 of the cassettes 24, 24a. The batteries 44 can therefore save electric power stored therein.

Figure 9:
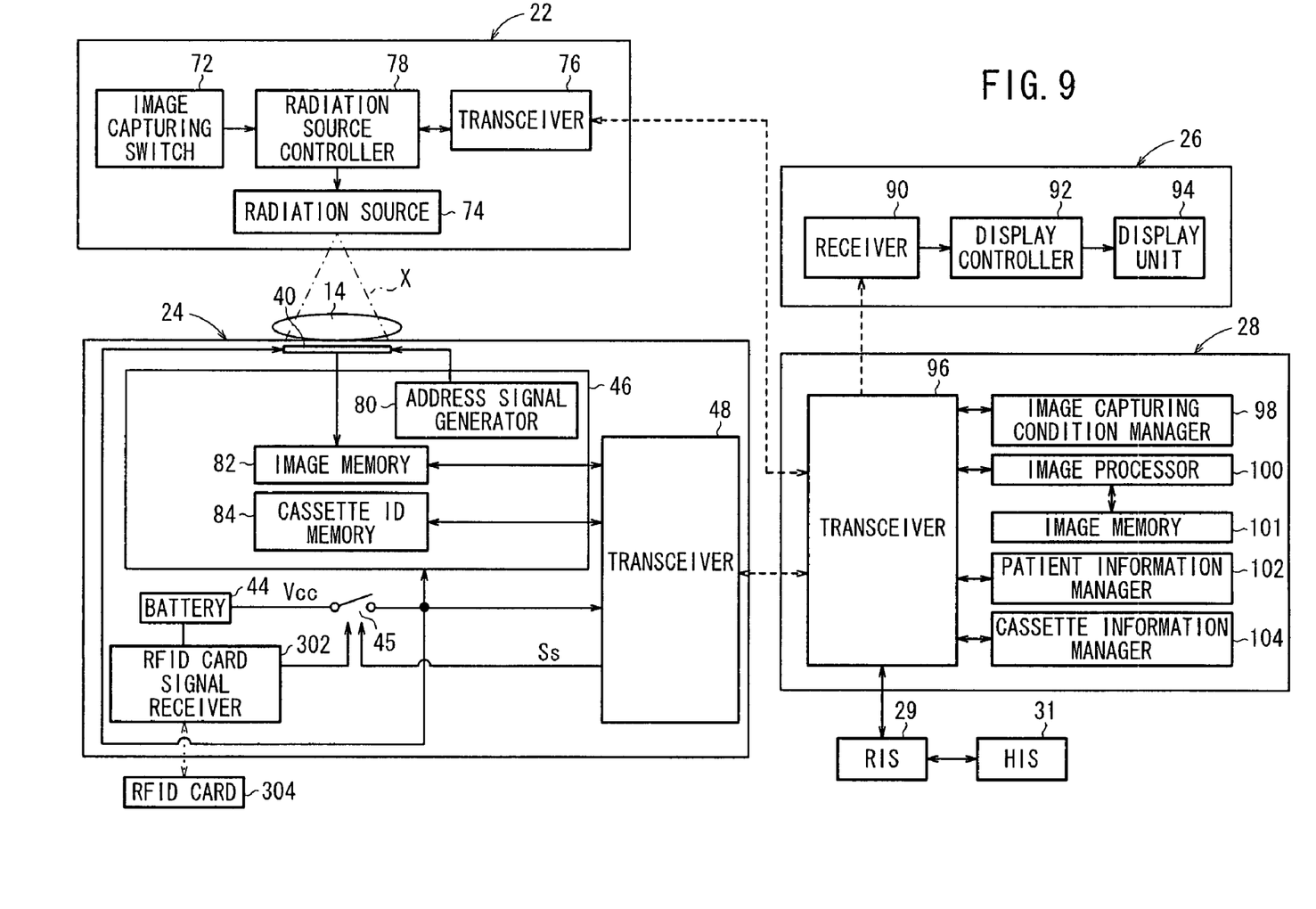
FIG. 9 is a block diagram of a radiation image capturing system according to still another embodiment of the present invention.

FIG. 9 shows in block form a radiation image capturing system according to still another embodiment of the present invention. In the radiation image capturing system shown in FIG. 9, the power supply switch 45 is turned on in step S1 (see FIG. 7) before starting to capture a radiation image when one of the surgeons 18 or the radiological technicians places an RFID (Radio Frequency IDentification) card 304 for authenticating themselves over an RFID card signal receiver (RFID signal transceiver) 320 provided in the cassette 24 to send an RFID signal to the RFID card signal receiver 320 by way of wireless communications.

In the radiation image capturing systems according to the embodiments, the radiation detector 40 housed in the cassette 24 directly converts the dose of the applied radiation X into an electric signal with the photoelectric conversion layer 51. However, the radiation image capturing systems may employ a radiation detector including a scintillator for converting the applied radiation X into visible light and a solid-state detecting device such as of amorphous silicon (a-Si) or the like for converting the visible light into an electric signal (see Japanese Patent No. 3494683).

Alternatively, the radiation image capturing systems may employ a light-conversion radiation detector for acquiring radiation image information. The light-conversion radiation detector operates as follows: When a radiation is applied to a matrix of solid-state detecting devices, the solid-state detecting devices store an electrostatic latent image depending on the dose of the applied radiation. For reading the stored electrostatic latent image, reading light is applied to the solid-state detecting devices to cause the solid-state detecting devices to generate an electric current representing radiation image information. When erasing light is applied to the radiation detector, radiation image information representing a residual electrostatic latent image is erased from the radiation detector, which can thus be reused (see Japanese Laid-Open Patent Publication No. 2000-105297).

When the cassette 24 is used in the operating room 12 or the like, blood stains and contaminants may be applied to the cassette 24. The cassette 24 may be of a water-resistant, sealed structure so that it can be sterilized and cleaned to remove such blood stains and contaminants for repetitive use.

The cassette 24 is not limited to being used in the operating room 12, but may be used in combination with medical examinations and doctor's visits to patient rooms in the hospital.

The cassette 24 and an external device may communicate with each other by way of optical wireless communications using infrared rays or the like, rather than usual wireless communications using radio waves.

Figure 10:
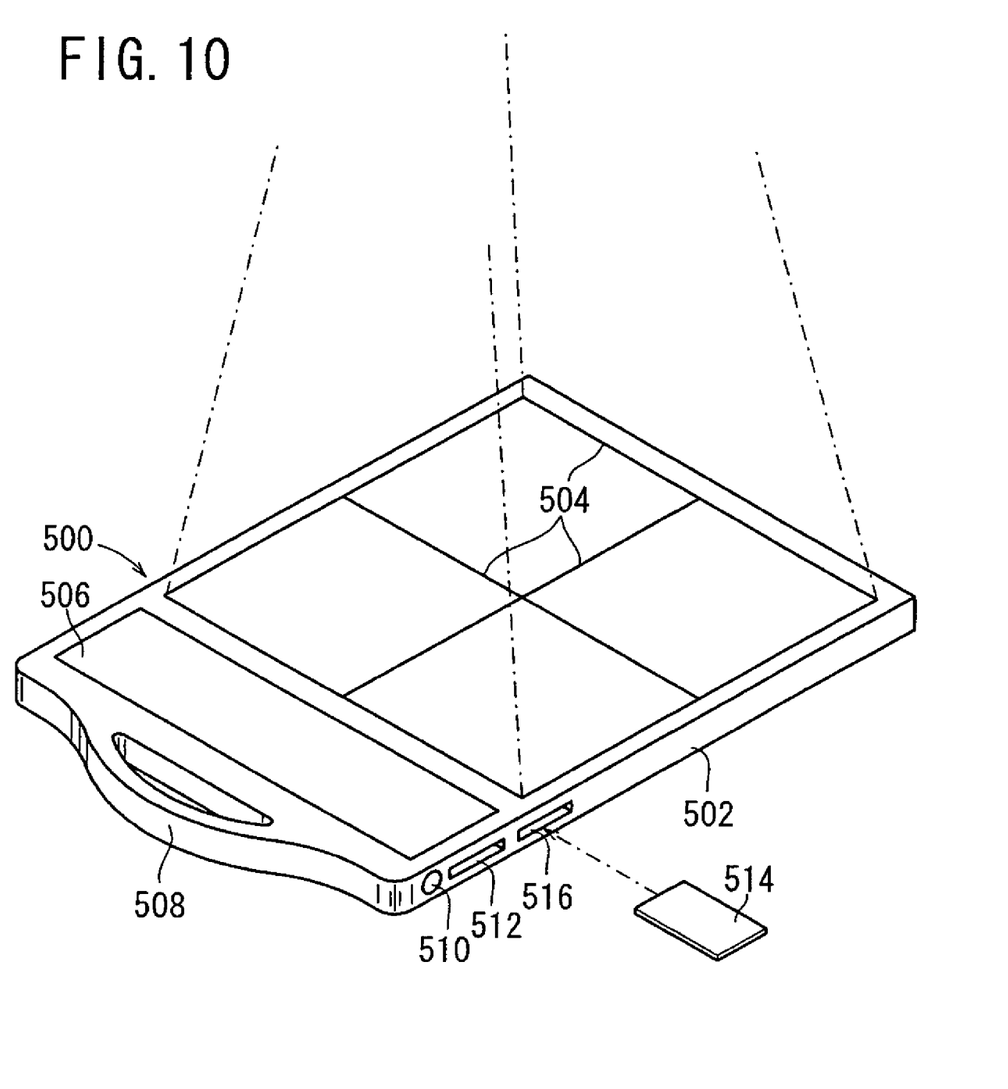
FIG. 10 is a perspective view of a cassette according to yet another embodiment of the present invention.

FIG. 10 shows in perspective a cassette 500 according to yet another embodiment of the present invention.

As shown in FIG. 10, the cassette 500 has guide lines 504 drawn on the irradiated surface of a casing 502 as a reference mark for an image capturing area and an image capturing position. Using the guide lines 504, the subject to be imaged, such as the patient 14, can be positioned with respect to the cassette 500 and the range in which the radiation is to be applied to the cassette 500 can be determined, for thereby recording radiation image information in an appropriate image capturing area of the cassette 500.

The cassette 500 also has a display unit 506 outside of the image capturing area thereof for displaying various items of information about the cassette 500. Specifically, the display unit 506 displays ID information of the subject, e.g., the patient 14, whose radiation image is recorded in the cassette 500, the number of times that the cassette 500 has been used, an accumulated exposed dose, the charged state (remaining power level) of the battery 44 housed in the cassette 500, image capturing conditions for radiation image information, and a positioning image representing the patient 14 positioned with respect to the cassette 500, etc. The radiological technician can confirm the patient 14 based on the ID information displayed on the display unit 506, also confirm in advance that the cassette 500 is in a usable state, position the desired area of the patient 14 to be imaged with respect to the cassette 500 based on the displayed positioning image, and capture optimum radiation image information in the cassette 500.

The cassette 500 includes a handle 508 to be gripped by the user to handle and carry the cassette 500 with ease.

The cassette 500 also has an input terminal 510 for connection to an AC adapter, a USB (Universal Serial Bus) terminal 512, and a card slot 516 for receiving a memory card 514, all provided on a side wall of the casing of the cassette 500.

When the charging function of the battery 44 housed in the cassette 500 is low or when there is not enough time to charge the battery 44, an AC adapter is connected to the input terminal 510 to supply electric power from an external source for thereby making the cassette 500 immediately operable.

The USB terminal 512 or the card slot 516 can be used when the cassette 500 is unable to send and receive information to and from an external device such as the console 28 or the like by way of wireless communications. Specifically, when a USB cable connected to the external device is connected to the USB terminal 512, the cassette 500 can send and receive information to and from the external device by way of wired communications through the USB terminal 512 and the USB cable. Alternatively, the memory card 514 is inserted into the card slot 516 and necessary information from the cassette 500 is recorded into the memory card 514. Thereafter, the memory card 514 is discharged from the card slot 516 and inserted into the external device so as to transfer the information to the external device.

Figure 11:
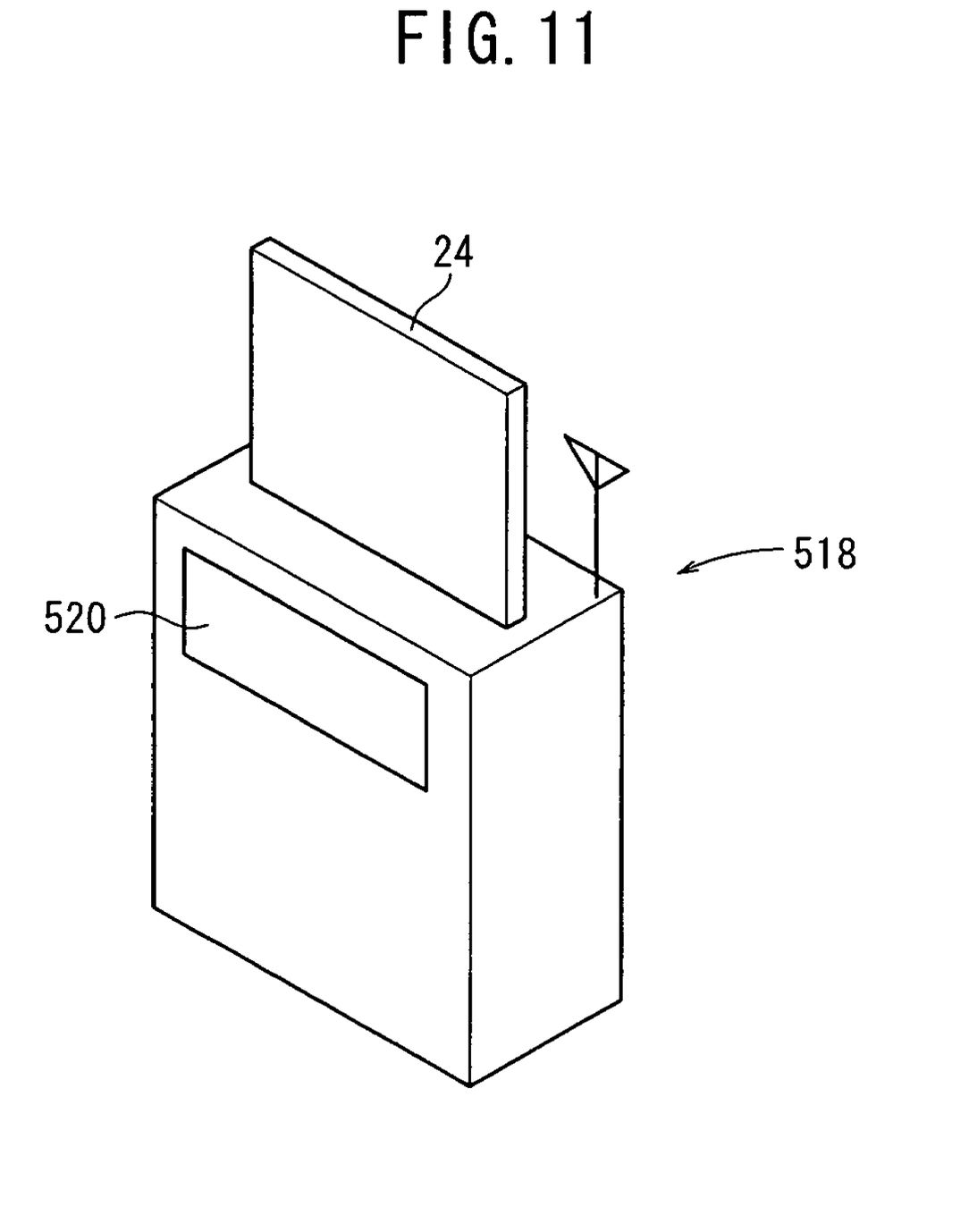
FIG. 11 is a perspective view of a cradle for charging a battery in the cassette.

FIG. 11 shows a cradle 518 for receiving the cassette 24, 24a and charging the battery 44 housed in the cassette 24, 24a. The cradle 518 is positioned in the operating room 12 or a desired location in the hospital. The cradle 518 may not only be able to charge the battery 44, but also have a wireless or wired communication function to send and receive necessary information to and from an external device, such as the RIS 29, the HIS 31, the console 28, or the like. The information that is sent from the cradle 518 may include radiation image information recorded in the cassette 24 loaded in the cradle 518.

The cradle 518 has a display unit 520 for displaying the charged state of the battery 44 housed in the cassette 24, 24a and necessary information including radiation image information acquired from the cassette 24, 24a.

A plurality of cradles 518 may be connected to a network, and charged states of the batteries 44 housed in the cassettes 24, 24a loaded in the respective cradles 518 may be retrieved through the network, so that the user can confirm the locations of any cassettes 24 whose batteries 44 are sufficiently charged, based on the retrieved charged states of the batteries 44.

Although certain preferred embodiments of the present invention have been shown and described in detail, it should be understood that various changes and modifications may be made therein without departing from the scope of the appended claims.

What is claimed is:

1. A radiation image capturing system comprising:

a cassette having a radiation detector for detecting a radiation that has passed through a subject and converting the detected radiation into radiation image information, an image memory for storing the converted radiation image information, a first transceiver for transmitting the radiation image information stored in said image memory to an external controller by way of wireless communications at a transmission radio-field intensity based on a command radio wave from the external controller, and a battery for supplying electric power to said radiation detector and the first transceiver; and the external controller having a second transceiver for transmitting said command radio wave and receiving the radiation image information transmitted from said cassette;

wherein when said first transceiver of the cassette starts to transmit the radiation image information to said second transceiver of the external controller, said first transceiver transmits a test radio wave, and said second transceiver calculates a minimum transmission radio-field intensity of said first transceiver which is required to receive the radiation image information, from a received intensity of said test radio wave, and transmits the command radio wave representing a command indicative of the calculated minimum transmission radio-field intensity to said first transceiver.

2. A radiation image capturing system according to claim 1, wherein said second transceiver transmits said command radio wave representing the command indicative of a radio-field intensity representative of the sum of the calculated minimum transmission radio-field intensity and a given radio-field intensity, to said first transceiver.

3. A radiation image capturing system according to claim 1, wherein said cassette includes a power supply switch, and said first transceiver transmits the test radio wave when said power supply switch is turned on.

4. A radiation image capturing system according to claim 3, wherein if said power supply switch has been turned on, said cassette turns off said power supply switch when said first transceiver finishes transmitting the radiation image information to said second transceiver.

5. A radiation image capturing system according to claim 3, wherein said cassette further includes an RFID signal receiver, and said power supply switch is turned on when an authenticated RFID card is placed over said RFID signal receiver.

6. A radiation image capturing system according to claim 3, wherein said power supply switch of said cassette is turned on in response to a turn-on command transmitted from the external controller via said second transceiver.

7. A radiation image capturing system according to claim 6, wherein when the transmission of the radiation image information is completed, said cassette turns off said power supply switch while said first transceiver is supplied with standby electric power.

8. A radiation image capturing system according to claim 1, further comprising an image capturing apparatus for applying said radiation at a dose according to image capturing conditions to said subject, wherein said external controller comprises a console for supplying said image capturing conditions to said image capturing apparatus.

9. A radiation image capturing system according to claim 8, wherein said console supplies said image capturing conditions to said image capturing apparatus via said second transceiver by way of wireless communications.

10. A method of setting a minimum transmission radio-field intensity in a radiation image capturing system when a cassette transceiver of a cassette having a radiation detector for detecting a radiation that has passed through a subject and converting the detected radiation into radiation image information starts to transmit the radiation image information to a console transceiver of a console, said method comprising the steps of:

transmitting a test radio wave from the cassette transceiver;

calculating, in the console transceiver, a minimum transmission radio-field intensity of said cassette transceiver which is required to receive the radiation image information, from a received intensity of said test radio wave, and transmitting a command radio wave representing the calculated minimum transmission radio-field intensity as a command from said console transceiver to said cassette transceiver; and setting a transmission radio-field intensity of said cassette transceiver to said minimum transmission radio-field intensity when said cassette transceiver receives said command radio wave, for transmitting the radiation image information at said minimum transmission radio-field intensity from said cassette transceiver to said console transceiver.

* * * * *